United States Patent
Saeed Bhatti et al.

(10) Patent No.: US 10,857,110 B2
(45) Date of Patent: Dec. 8, 2020

(54) ANTIBACTERIAL COMPOUNDS

(71) Applicants: CONSEJO NACIONAL DE INVESTIGACIONES CIENTÍFICAS Y TÉCNICAS (CONICET), Ciudad Autónoma de Buenos Aires (AR); UNIVERSIDAD NACIONAL DE LA PLATA (UNLP), La Plata (AR); QUAID-I-AZAM UNIVERSITY, Islamabad (PK)

(72) Inventors: Aamer Saeed Bhatti, Islamabad (PK); María Alejandra Nieves Bosch, City Bell (AR); Yanina Andrea Lamberti, La Plata (AR); Mauricio Federico Erben, La Plata (AR)

(73) Assignees: CONSEJO NACIONAL DE INVESTIGACIONES CIENTIFICAS Y TECNICAS (CONICENT), Ciudad Autónoma de Buenos Aires (AR); UNIVERSIDAD NACIONAL DE LA PLATA (UNLP), La Plata (AR); QUAID-I-AZAM UNIVERSITY, Islamabad (PK)

(*) Notice: Subject to any disclaimer, the term of this patent is extended or adjusted under 35 U.S.C. 154(b) by 123 days.

(21) Appl. No.: 16/324,509

(22) PCT Filed: Aug. 9, 2017

(86) PCT No.: PCT/IB2017/054870
§ 371 (c)(1),
(2) Date: Feb. 8, 2019

(87) PCT Pub. No.: WO2018/029618
PCT Pub. Date: Feb. 15, 2018

(65) Prior Publication Data
US 2019/0167609 A1 Jun. 6, 2019

(30) Foreign Application Priority Data

Aug. 11, 2016 (AR) .............. 20160102465

(51) Int. Cl.
*A61K 31/155* (2006.01)
*A61P 31/04* (2006.01)
*C07C 279/18* (2006.01)

(52) U.S. Cl.
CPC ........... *A61K 31/155* (2013.01); *A61P 31/04* (2018.01); *C07C 279/18* (2013.01)

(58) Field of Classification Search
None
See application file for complete search history.

(56) References Cited

FOREIGN PATENT DOCUMENTS

WO WO 2004/073709 A1 9/2004

*Primary Examiner* — Jared Barsky
(74) *Attorney, Agent, or Firm* — Muncy, Geissler, Olds & Lowe, P.C.

(57) ABSTRACT

An antibacterial compound of formula I, wherein X is selected from fluoro or bromo, effective against Gram negative and Gram positive bacteria, and in particular against non-fermenting multiresistant bacteria affecting patients suffering from cystic fibrosis and which are responsible of severe hospital-acquired infections in immunodepressed patients; its preparation process and pharmaceutical composition comprising said compound.

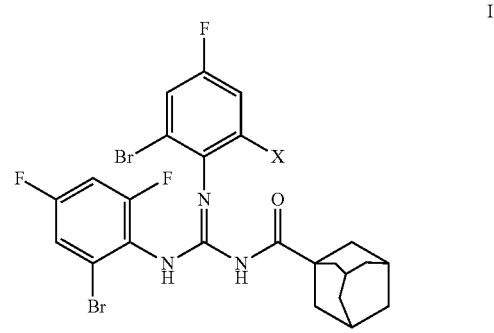

11 Claims, No Drawings

ANTIBACTERIAL COMPOUNDS

TECHNICAL FIELD

The instant invention encompasses new guanidine-derived compounds with antibacterial activity against multiresistant, non-fermenting Gram-negative bacilli. In particular, these compounds are useful in the treatment of patients suffering from cystic fibrosis, severe hospital-acquired infections, and immunodepressed patients.

BACKGROUND OF THE INVENTION

Among the prior art for this invention are previous works which analyzed the antimicrobial activity against different bacterial strains of a number of guanidine-like compounds. None of these previous works studied the antimicrobial activity against multiresistant strains of the respiratory tract which currently infect and are a serious concern in the treatment of patients which are immunocompromised, suffering from cystic fibrosis, or suffering from hospital-acquired infections. This prior art is discussed below.

Murtaza et al. studied the antimicrobial activity of guanidine-like compounds, in particular of benzoyl-substituted guanidines, against the Gram (+) bacteria *Staphylococcus aureus* and *Micrococcus luteus*, and the Gram (−) bacteria *Salmonella setubal*. While the antimicrobial activity of these compounds is acceptable, it is below that of commercially available antibiotics. Murtaza et al. do not analyze the activity of these compounds against multiresistant strains (Murtaza, G.; Rauf, M. K.; Badshah, A.; Ebihara, M.; Said, M.; Gielen, M.; De Vos, D.; Dilshad, E.; Mirza, B., Eur. J. Med. Chem. 2012, 48, 26-35).

The patent application WO 2004073709 A1 discloses tertiary amines, some of which contain guanidine groups, as antimicrobial agents. Its bactericidal action against *Escherichia coli* and *Bacillus subtilis* and antifungal action against *Saccharomyces cereviseae* was determined. However, these guanidines are chemically different from those of the instant invention and its antimicrobial activity against multiresistant strains of the respiratory tract is not evaluated.

Hensler et al. reported the synthesis of a group of guanidines containing pyrrolidine groups, chemically different from those of the instant invention, which have shown high antimicrobial activity against multiresistant species such as *Staphylococcus aureus* (MRSA) and *Enterococcus faecalis* (VRE) (Hensler, M. E.; Bernstein, G.; Nizet, V.; Nefzi, A., Bioorganic & Medicinal Chemistry Letters 2006, 16, 5073-5079). It has been shown also that the salts of some guanidine compounds, generally in its chloride salts, have antimicrobial activity against antibiotic-resistant bacterial strains, such as *Staphylococcus aureus*, Staphylococci, *Enterococcus faecium* and *P. aeruginosa* (Sun, S.; An, Q.; Li, X.; Qian, L.; He, B.; Xiao, H., Bioresource Technology 2010, 101, 5693-5700).

It has been reported that some guanidine and thioguanidine compounds can be used as pro-drugs of compounds with therapeutic properties, in particular as enzyme inhibitors (EP 0743320 A2).

It has been reported also that the acyl guanidine derivatives have in vitro antibactericidal activity against a number of strains, including *Escherichia coli, Klebsiella pneumoniae, Staphylococcus aureus, Staphylococcus epidermidis* and *Bacillus subtilis*. Inhibition area assays have shown that these compounds have higher antibacterial activity than the antibiotic streptomycin, except for *S. aureus*. The Minimum Inhibitory Concentration (MIC) values for *E. coli* and *B. subtilis* were 77 and 80 µg/ml respectively on average, with small variations among the analyzed compounds (Said, M., A. Badshah, N. Shah, H. Khan, G. Murtaza, B. Vabre, D. Zargarian, M. Khan. 2013. Molecules 18:10378. Said, M., J. Ahmad, W. Rehman, A. Badshah, et al. 2015. Inorg. Chim. Acta 434:7).

The methods for chemical synthesis of guanidines were reviewed by Katritzky and Rogovoy (Arkivoc 2005, iv, 47-87). The compounds of the instant invention were prepared for the first time by the inventors, using a general synthesis method adapted from a previously reported process (S. Cunha, M. I. s. B. Costa, H. B. Napolitano, C. Lariucci and I. Vencato, Tetrahedron, 2001, 57, 1671-1675).

Patent application WO2004073709 ("Antimicrobial Agents"), discloses the synthesis of tertiary amines, including guanidine derivatives, with antimicrobial activity against bacteria and fungi.

Patent application US 2001/0023251 A1 ("Guanidine Derivatives, Processes for Preparing Them and Their Use as Pharmaceutical Compositions") discloses the synthesis of new guanidine derivatives and pharmaceutical composition thereof which have antimicrobial activity (including against pathogens associated with cystic fibrosis), antiviral and anti-inflammatory activity, and especially as sphingomyelinase inhibitors.

As noted above, there are recent publications where the antibacterial activity of similar chemical compounds is also shown, for example:

Murtaza, G., M. K. Rauf, A. Badshah, M. Ebihara, et al. 2012. Eur. J. Med. Chem. 48:26.

Hensler, M. E., G. Bernstein, V. Nizet, A. Nefzi. 2006. Bioorg. Med. Chem. Lett. 16:5073.

Said, M., A. Badshah, N. Shah, H. Khan, G. Murtaza, B. Vabre, D. Zargarian, M. Khan. 2013. Molecules 18:10378.

Said, M., J. Ahmad, W. Rehman, A. Badshah, et al. 2015. Inorg. Chim. Acta 434:7.

G. Murtazar dissertation (Synthesis, Characterization and Biological Studies of Novel Guanidines and Their Complexes, Quaid-i-Azam University, Islamabad, Pakistan) discloses the preparation of acyl guanidines and its cupper complexes, and analyzes its biologic activity on fungi, parasites (leishmaniasis) and its in vitro enzymatic activity.

However, none of the aforementioned publications discloses the compounds of the instant invention, nor its easy and efficient preparation, and in particular the in vitro results regarding its antibacterial activity.

The new guanidines of the instant invention, represented in FIG. 1 and obtained by means of chemical synthesis, are of formula $C_{24}H_{21}XBr_2F_3N_3O$, wherein X is Br (compound code H-DBF) or F (compound code H-BDF), show a proven in vitro antibacterial activity against Gram-positive organisms (*Bacillus cereus, Stapyloccocus aureus*), fermenting Gram-negative (*Escherichia coli*) and multiresistant non-fermenting Gram-negative (*Pseudomonas aeruginosa, Inquilinus limosus, Bordetella bronchiseptica*, species from the complex *Burkholderia cepacia*, among others).

BRIEF DESCRIPTION OF THE INVENTION

The antibacterial compound which is object of this invention has the formula I

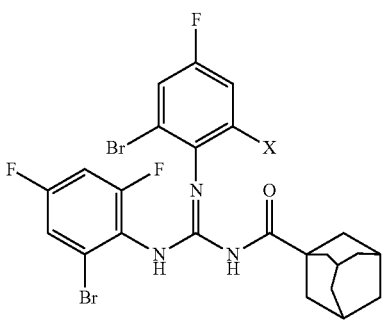

I wherein X is selected from fluoro or bromo.

It is another object of the invention a process for preparing the antibacterial compound of Formula I of the invention, the process comprising the steps of:
a) adding an amine and trietilamine to an acyl thiourea in solvent; wherein said acyl thiourea is preferably the acyl thiourea represented by the formula II

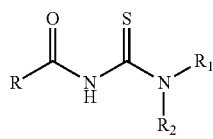

II wherein R is the adamantyl group $C_{10}H_{15}$, $R_1$ is H and $R_2$ is 2-Br-4,6-$F_2$—$C_6H_2$;
and said solvent is preferably dimethylformamide;
b) slowly adding $HgCl_2$ to the mixture of step a);
c) allowing the reaction to proceed at room temperature for at least 6 hours;
wherein said amine of step a is $R_3$—$NH_2$, wherein $R_3$ is selected from the group comprising 2-bromo-4,6-difluoro phenyl (2-Br,4,6-$F_2$—$C_6H_2$) and 2,6-dibromo-4-fluoro phenyl (2,6-$Br_2$, 4-F—$C_6H_2$); and steps a and b are preferably carried out under agitation and with a cold source as to prevent the temperature from rising.

The instant invention also provides a purification process after step c, by which the compound of the invention is obtained as a purified guanidine with a purity higher than 95%, through the following additional steps:
d) removing by filtration the HgS formed during the reaction, which is an highly insoluble solid;
e) removing by filtration the $Et_3NH^+Cl^-$ salt, which is the other solid formed during the reaction, by an extraction process consisting of water addition and ethyl acetate to the reaction mixture under vigorous agitation;
f) allowing to settle and separating the ethyl acetate organic layer;
g) optionally, repeating three times the extraction process of steps e) and f);
h) drying the organic phase by adding $MgSO_4$ or $CaCl_2$ and removing the solvent under negative pressure;
i) the obtained solid is purified by standard ethanol re-crystallization methods.

It is another object of the invention a pharmaceutical bactericidal composition (against Gram-positive and Gram-negative bacteria) comprising the compound of the invention. It is another object of the invention a pharmaceutical composition comprising the compound of the invention for treatment of respiratory infections in cystic fibrosis patients.

It is another object of the invention a pharmaceutical composition comprising the compound of the invention for treatment of multiresistant infections preferably against non-fermenting Gram-negative bacteria.

DETAILED DESCRIPTION OF THE INVENTION

The new compounds of the invention were synthesized following the general method of preparation (Tetrahedron, 2001, 57, 1671-1675), from the reaction between an intermediary compound of the acyl thiourea and $HgCl_2$ in presence of trimethylamine. The products were adequately characterized regarding its chemistry. The antibacterial activity of the new compounds was assayed against two Gram-positive reference strains: *Staphylococcus aureus* (ATCC6538) and *Bacillus cereus* (ATCC10876), a fermenting Gram-negative strain: *Escherichia coli* (ATCC25922), and 26 non-fermenting Gram-negative isolates, including 3 reference strains: *Pseudomonas aeruginosa* (PAO1), *Bordetella bronchiseptica* (9.73H+), and *Inquilinus limosus* (DSM16000), and 23 isolates recovered from patients suffering from cystic fibrosis, including one *Achromobacter xylosoxidans* isolate, and 22 isolates belonging to the *Burkholderia cepacia* complex. The later were selected because they presented resistance to a high number of antimicrobial compounds, among a panel of 125 clinical isolates previously analyzed for its resistance against 17 antimicrobial compounds (1,2). The antibiotic sensitivity studies were performed by applying two quantitative methods which allow to determine the minimum inhibitory concentration (MIC) and the minimum bactericidal concentration (MBC).

The studies indicate that both compounds have MIC and MBC values similar or lower than those found using commercially available antibiotics. As an example, the in vitro biologic assays showed that compound H-BDF has a MIC of 3.9 µg/ml and a MBC of 7.81 µg/ml against *Burkholderia seminalis* (CBC 040). This strain is resistant to most commercial antibiotics, namely: ampicillin, ampicillin-sulbactam, piperazine-tazobactam, cefalotin, cefoxitin, cefotaxim, ceftazidime, cefepime, imipenem, meropenem, amikacin, gentamicin, nalidixic acid, ciprofloxacin, nitrofurantoin, colistin and trimethoprim-sulfametazole (1).

The activity observed for the compound of the invention is either similar or superior to the antibiotics prescribed with the regular treatments.

The antimicrobial activity of compound H-BDF is similar or even superior to the activity reported for other guanidine-derived compounds against a number of Gram-positive and Gram-negative strains. For example, the MIC values for *E. coli* of the guanidine derivatives disclosed in patent application WO 2004073709 A1 are higher than 1 µg/ml. The guanidine derivatives disclosed by Hensler and colleagues (Hensler, M. E.; Bernstein, G.; Nizet, V.; Nefzi, A., Bioorganic & Medicinal Chemistry Letters 2006, 16, 5073-5079) have MIC values higher than 2.5 µg/ml against *E. coli*. The MIC values against *E. coli* of the guanidine salts disclosed by Sun and colleagues (Sun, S.; An, Q.; Li, X.; Qian, L.; He, B.; Xiao, H., Bioresource Technology 2010, 101, 5693-5700) are between 8 and 16 µg/ml. Compound H-BDF of this invention has MIC values against *E. coli* which are similar or lower than the aforementioned compounds (0.97 µg/ml). In vitro cytotoxicity assays were performed using the human monocyte cell line THP-I and vital staining with Trypan Blue (3). The IC50 value was defined as the higher drug concentration at which 50% of cells are viable compared with the control. These studies showed that the assayed compounds have a low to moderate cytotoxicity level (H-BDF: IC50=15.25 µg/mL µM; H-DBF: IC50>132.5 µg/mL). The Selectivity Index (SI), defined as the ratio between the IC50 and the MIC for each compound, was calculated. Compound H-BDF has an SI>10, which makes it a good antimicrobial candidate according to the criteria set up by Orme (5).

It is an object of the invention a process for the synthesis of two new chemical compounds, namely H-DBF and H-BDF, which are powerful antimicrobial agents against non-fermenting Gram-negative multiresistant bacilli isolated from patients suffering from cystic fibrosis, immunocompromised or affected by a hospital-acquired infection.

From the chemical point of view, compounds H-DBF and H-BDF belong to the chemical family of the acyl guanidines. Although the chemical synthesis general method for guanidines is well known (see for example Tetrahedron, 2001, 57, 1671-1675), the compounds of the invention are new, i.e. were unknown before this invention.

In in vitro assays, compounds H-DBF and H-BDF showed to be effective against bacteria which were multiresistant to most of the currently used antibiotics, notably against *Pseudomonas aeruginosa, Achromobacter xylosoxidans, Inquilinus limosus* and species from the *Burkholderia cepacia* complex (*B. cepacia, B. cenocepacia, B. seminalis, B. multivorans* and *B. contaminans*). To the date, no studies have shown bactericidal activity of similar compounds against multiresistant strains such as those presented in this application.

In the instant invention, compounds H-DBF and H-BDF have antimicrobial properties with minimum inhibitory concentration (MIC) values and minimum bactericidal concentration (MBC) much lower to those reported in previous studies for similar compounds, with values similar or lower than those calculated using commercially available antibiotics typically used for treating these kinds of infections (meropenem, tobramycin, ceftazidime). It has been shown that the composition of the instant invention has an outstanding antimicrobial effect against multiresistant strains from the respiratory tract which threaten patients affected by cystic fibrosis, immunodepressed or suffering from severe hospital acquired infection, including those by the species *Pseudomonas aeruginsa, Achromobacter xylosoxidans, Inquilinus limosus* and species from the *Burkholderia cepacia* complex (*B. cepacia, B. cenocepacia, B. seminalis, B. multivorans* and *B. contaminans*). These activity levels against multiresistant isolates have not been shown before for compounds of this kind (guanidines).

The low cytotoxicity of compounds H-DBF and H-BDF is yet another remarkable advantage of the compounds of the invention relative to the prior art compounds. In vitro assays in human tumor cells show that the compounds of the invention have low to moderate cytotoxicity levels. The SI values of compounds H-BDF and H-DBF against *S. aureus* are 62 and 17, respectively, whereas the SI values for *E. coli*, are 16 and 2, respectively. This means that these compounds can be considered as good antibacterial agents according to the criteria set up by Orme (5).

The chemical synthesis steps leading to the compounds of the invention as final product are easily performed, with a high reaction yield. Purification of the products is carried out by the usual processes of organic chemistry. The compounds of the invention are stable over an extended period of time and its storage conditions do not have particular requirements.

The compounds of the invention are effective against bacterial strains which usually compromise the pulmonary function in patients suffering from cystic fibrosis, as demonstrated in in vitro assays. These compounds could represent a therapeutic alternative in the fight against the aforementioned infections, whose treatment is usually difficult and has a low rate of success due to the high resistance level presented by these strains to the commonly used antibiotics. Cytotoxicity assays based on the human monocyte cell line THP-I demonstrate that the compounds of the invention have a moderate to low toxicity level.

The compounds of the invention have been characterized using the standard techniques, including elementary chemistry analysis, melting point, infrared spectroscopy, and nuclear magnetic resonance spectroscopy.

The method used in the synthesis of compounds H-BDF and H-DBF is explained in further detail below, according to the synthesis reaction outlined below:

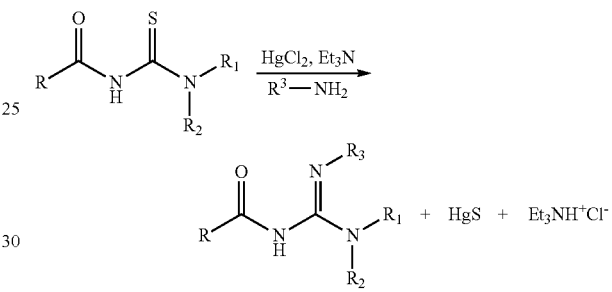

An amount of acyl thiourea is placed in a reaction container (R=adamantyl $C_{10}H_{15}$, $R_1$=H, $R_2$=2-Br-4,6-$F_2$—$C_6H_2$) in dimethyl formamide solvent. This system is kept under agitation in cooling bath, and a weighted amount of the corresponding $R_3NH_2$ amine (2-bromo-4,6-difluoro aniline ($R_3$=2-Br-4,6-$F_2$—$C_6H_2$) for H-BDF, and 2,6-dibromo-4-fluoro aniline ($R_3$=2,6-$Br_2$-4-F—$C_6H_2$) for H-DBF) and trimethylamine [$(CH_3CH_2)_3N$] are added in succession. The reaction conditions are mild, slowly adding the $HgCl_2$ to the reaction mixture kept under refrigeration by using refrigeration means and keeping the system under agitation for at least 6 hours, preferably 12 hours at room temperature. The reaction progress can be tracked by thin layer chromatography using a mixture of n-hexane/ethyl acetate at a ratio 10:1 as solvent.

The purification process for the guanidines is relatively simple. As it is well known in the art, HgS is a highly insoluble solid which can be easily removed from the reaction medium by filtration. The other by-product of the invention, the $Et_3NH^+Cl^-$ salt, is removed by an extraction process consisting of the addition of water and ethyl acetate to the reaction mixture under strong agitation. After settling, the organic phase containing the ethyl acetate is separated. The extraction process is repeated three times, the organic phase is dried by addition of $MgSO_4$ or $CaCl_2$, and the solvent is removed under reduced pressure. The obtained solid is purified by standard ethanol recrystallization methods. This preparation method allows for high yields (70%) and the purity of the obtained product generally is higher than 95% as measured through nuclear magnetic resonance spectroscopy. If needed, the reaction product can be purified by silica gel column chromatography, using n-hexane/acetate at a 10:1 ratio as elution solvent.

EXAMPLES

Example 1

Preparation of H-DBF (Formula $C_{24}H_{21}Br_3F_3N_3O$)

A weighted amount (10 mmol) of acyl thiourea of formula II (R=adamantyl, $R_1$=H, $R_2$=2-Br-4,6-$F_2$—$C_6H_2$) was placed in a reaction container in dimethyl formamide solvent (20 mL). The system was kept under agitation in ice bath, and a weighted amount of the corresponding $R_3NH_2$ amine ($R_3$=2,6-$Br_2$-4-F—$C_6H_2$) (10 mmol) and trimethylamine [$(CH_3CH_2)_3N$] (20 mmol) were added in succession. The reaction conditions were mild, slowly adding the $HgCl_2$ to the reaction mixture kept in ice bath and keeping the system under agitation for 12 hours at room temperature. The reaction progress was tracked by thin layer chromatography using a mixture of n-hexane/ethyl acetate at a 10:1 ratio as solvent.

HgS is a highly insoluble solid which was removed from the reaction medium by filtration. The other reaction by-product, the $Et_3NH^+Cl^-$ salt, was removed by an extraction process consisting of the addition of 5 ml of water and 5 ml of ethyl acetate to the reaction mixture under strong agitation. After settling, the organic phase containing the ethyl acetate was separated. The extraction process was repeated three times, the organic phase was dried by addition of $MgSO_4$, and the solvent was removed under reduced pressure. The obtained solid was purified by standard ethanol recrystallization methods. This preparation method allowed for high yields (70%) and a purity of the obtained product which was higher than 95% as measured through nuclear magnetic resonance spectroscopy.

Example 2

Preparation of H-BDF (Formula $C_{24}H_{21}Br_2F_4N_3O$)

A weighted amount (10 mmol) of acyl thiourea was placed in a reaction container (R=adamantyl $C_{10}H_{15}$, $R_1$=H, $R_2$=2-Br-4,6-$F_2$—$C_6H_2$) in dimethyl formamide solvent (20 mL). The system was kept under agitation in ice bath, and a weighted amount of the corresponding $R_3NH_2$ ($R_3$=2-Br-4,6-$F_2$—$C_6H_2$) (10 mmol) and triethylamine [$(CH_3CH_2)_3N$] (20 mmol) were added in succession. The reaction conditions were mild, slowly adding the $HgCl_2$ to the reaction mixture kept in ice bath and keeping the system under agitation for 12 hours at room temperature. The reaction progress was tracked by thin layer chromatography using a mixture of n-hexane/ethyl acetate at a 10:1 ratio as solvent.

HgS is a highly insoluble solid which was removed from the reaction medium by filtration. The other reaction by-product, the $Et_3NH^+Cl^-$ salt, was removed by an extraction process consisting of the addition of 5 ml of water and 5 ml of ethyl acetate to the reaction mixture under strong agitation. After settling, the organic phase containing the ethyl acetate was separated. The extraction process was repeated three times, the organic phase was dried by addition of $CaCl_2$, and the solvent was removed under reduced pressure. The obtained solid was purified by standard ethanol recrystallization methods. This preparation method allowed for high yields (70%) and a purity of the obtained product which was higher than 95% as measured through nuclear magnetic resonance spectroscopy. Further purification can be achieved by silica gel column chromatography using a mixture of n-hexane/ethyl acetate at a ratio 10:1 as eluting solvent.

Example 3

Chemical Characterization

The compounds synthesized in Examples 1 and 2 are solid at room temperature, stable, can be handled without any special care, and are unaffected when handled in presence of air and atmospheric humidity. Their melting point and elementary composition were determined. The compounds were characterized using Fourier transform infrared spectroscopy techniques (FT-IR) using the KBr pellet method and by multinuclear Nuclear Magnetic Resonance spectrometry ($^1H$ and $^{13}C$) in $CDCl_3$. The obtained data are summarized below:

N—(N,N'-bis(2-bromo-4,6-difluorophenyl)carbamimidoyl)adamantane-1-carboxamide (code H-BDF): yield of the reaction 70%, melting point 174° C. FT-IR (KBr, $cm^{-1}$): 3336, 3413, 3245, 3128, 3043, 3034, 2909, 2849, 1675, 1575, 1457, 1370. $^1H$ NMR (300 MHz, $CDCl_3$): δ 9.79 (br s, 1H, NH, interchangeable in $D_2O$); 8.04 (br s, 1H, NH, interchangeable in $D_2O$); 7.17-7.13 (m, 2H, Ar), 7.06-6.98 (m, 2H, Ar), 2.0 (br s, 3H, adamantane-H), 1.94-1.89 (br m, 3H, adamantane-H), 1.78-1.60 (br m, 10H, adamantane-H); $^{13}C$ NMR (75 MHz, $CDCl_3$): 178.2 (C=O), 174.2 (C=N), 154.9, 151.8, 148.6, 131.9, 114.6, 107.8, 103.2 (ArCs), 40.9, 37.9, 35.8, (adamantane-C); Estimated analysis for $C_{24}H_{21}F_4Br_2N_3O$ (603.0): C, 47.78; H, 3.51; N, 6.97%. Found: C, 48.1; H, 3.49; N, 7.01%.

N—(N-(2-bromo-4,6-difluorophenyl)-N'-(2,6-dibromo-4-fluorophenyl)carbamimidoyl) adamantane-1-carboxamide (code H-DBF) yield of the reaction 70%, mp 144° C. FT-IR (KBr, $cm^{-1}$): 3413, 3245, 3128, 3043, 3034, 2909, 2849, 1675, 1575, 1457, 1370. $^1H$ NMR (300 MHz, $CDCl_3$): δ 11.94 (br s, 1H, NH, interchangeable in $D_2O$); 9.66 (br s, 1H, NH, interchangeable in $D_2O$); 7.48 (m, 1H, Ar), 7.23 (m, 2H, Ar), 7.01 (m, 1H, Ar), 1.99-1.84 (m, 10H, adamantane-H), 1.79-1.59 (m, 6H, adamantane-H); $^{13}C$ NMR (75 MHz, $CDCl_3$): 179.2 (C=O), 174.2 (C=N), 160.4, 159.8, 157.2, 151.9, 147.2, 140.2, 123.9, 115.8, 114.3, 104.5 (ArCs), 41.9, 37.6, 35.8 (adamantane-C); Estimated analysis for $C_{24}H_{21}F_3Br_3N_3O$ (663.1): C, 43.40; H, 3.19; N, 6.33%. Found: C, 43.21.1; H, 3.52; N, 6.97%.

Example 4

In Vitro Assays

The compounds obtained in Examples 1 and 2 were assayed against 23 isolates recovered from the sputum of patients suffering from cystic fibrosis being treated at the Sor Maria Ludovica Children Hospital (La Plata, Buenos Aires, Argentina). Nineteen of these isolates were selected for being highly resistant to most of the antimicrobial agents of clinical use from a panel of 125 isolates previously characterized in Martina et al. (1). Reference strains were also included: Gram (+) bacteria: *B. cereus* and *S. aureus*, fermenting Gram (−) bacteria: *E. coli*, and non-fermenting Gram (−) bacteria: *Inquilinus limosus* (DSM16000), *B. bronchiseptica*, and *Pseudomonas aeruginosa* (PAO1). The antibiotic sensitivity studies were performed applying two quantitative methods which allow to determine the minimum inhibitory concentration (MIC) and the minimum bactericidal concentration (MBC) according to the criteria established by the Clinical and Laboratory Standards Institute (CLSI) (4). For comparative purposes, three antibiotics commonly used in the treatment of pulmonary infections in cystic fibrosis patients were included in the study: tobramycin, ceftazidime and meropenem. Results are shown in Table I below.

TABLE I

Microbial susceptibility of strains isolated from cystic fibrosis patients

| | H-BDF | | H-DBF | | Tobramucin | | Meropenem | | Ceftazimide | |
|---|---|---|---|---|---|---|---|---|---|---|
| | MIC | MBC | MIC | MBC | MIC | MBC | MIC | MBC | MIC | MBC |
| Reference strains | (µg/ml) | (µg/ml) | (µg/ml) | (µg/ml) | (µg/ml) | (µg/ml) | (µg/ml) | (µg/ml) | (µg/ml) | (µg/ml) |
| *B. branchisaptica* (9.73H+) | 0.48 | 1.95 | 16.6 | 66.5 | 62.5 | 62.5 | <0.48 | <0.48 | 7.81 | 62.5 |
| *S. aureus* (ATCC6538) | 0.24 | 0.97 | 7.81 | 66.4 | 1.95 | 1.95 | <0.48 | <0.48 | 7.81 | 7.81 |
| *Bacillus cereus* (ATCC10876) | 1.95 | 1.95 | 66.4 | 66.4 | 7.81 | 31.25 | <0.48 | <0.48 | 0.97 | 0.97 |
| *E. coli* (ATCC25922) | 0.97 | 1.95 | 66.4 | 66.4 | 15.62 | 15.62 | <0.48 | <0.48 | 0.97 | 0.97 |
| *P. aeruginosa* (PAO1) | 0.48 | 3.9 | 33.2 | >132.8 | 1.95 | 1.95 | <0.48 | <0.48 | 1.95 | 1.95 |
| *Inquilinus Ifmosus* (DSM16000) | 3.9 | 7.81 | 61.25 | nd | R | nd | <0.48 | <0.48 | R | nd |
| Clinical isolates[a] | | | | | | | | | | |
| *Burkholderia seminaliz* (CBC040) | 3.9 | 7.81 | 61.25 | >61.25 | R | nd | R | nd | R | nd |
| *B. cenacepacia* (FQC2524) | 0.97 | 3.9 | 15.62 | 31.25 | R | nd | S | nd | S | nd |
| *B. contaminans* (HNBC001) | <0.48 | 0.97 | 15.62 | 31.25 | R | nd | R | nd | S | nd |
| *Burkholderia cenocepacia* (HE001) | 3.9 | 61.25 | 61.25 | >61.25 | R | nd | R | nd | R | nd |
| *Achromobacter xylosaxidans* (HNA001) | <0.48 | <0.48 | 7.8 | 31.25 | R | nd | S | 7.81 | S | nd |
| *Burkholderia multivorans* (CBC 018) | 1.95 | 7.81 | 66.4 | >132 | R | nd | S | 3.9 | S | 7.81 |
| *Burkholderia cenocepacia* (CBC 023) | 1.95 | 3.9 | 66.4 | 132 | R | nd | R | nd | R | nd |
| *Burkholderia cenocepacia* (CBC 035) | 1.95 | 3.9 | 66.4 | 132 | R | nd | S | 15.62 | S | 15.62 |
| *Burkholderia cenocepacia* (CBC 036) | 1.95 | 7.81 | 66.4 | 132 | R | nd | R | nd | S | 15.62 |
| *Burkholderia multivorans* (CBC 015) | 1.95 | 3.9 | 66.4 | 132 | R | nd | S | 3.9 | S | 7.81 |
| *Burkholderia cenocepacia* (CBC 031) | 1.95 | 7.81 | 31.25 | 62.5 | R | nd | R | nd | S | 7.81 |
| *Burkholderia cenocepacia* (CBC 032) | 1.95 | 3.9 | 31.25 | 62.5 | R | nd | R | nd | S | 7.81 |
| *Burkholderia multivorans* (CBC 019) | 1.95 | 7.81 | 66.4 | 132 | R | nd | S | 7.81 | R | nd |
| *Burkholderia cenocepacia* (CBC 024) | 1.95 | 7.81 | 66.4 | 132 | R | nd | R | nd | S | 7.81 |
| *Burkholderia seminalis* (CBC 042) | 0.96 | 7.81 | 33.2 | 66.4 | R | nd | R | nd | R | nd |
| *Burkholderia multivorans* (CBC 016) | 1.95 | 7.81 | 66.4 | >132 | R | nd | R | nd | S | 3.9 |
| *Burkholderia multivorans* (CBC 021) | 1.95 | 3.9 | 66.4 | >132 | R | nd | S | 7.81 | R | nd |
| *Burkholderia cepacia* (CBC 010) | 3.9 | 7.81 | 132.8 | >132 | R | nd | S | 3.9 | R | nd |
| *Burkholderia cepacia* (CBC 011) | 1.95 | 30.16 | 66.4 | >132 | R | nd | S | >62.5 | R | nd |
| *Burkholderia multivorans* (CBC 020) | 3.9 | 15.62 | 66.4 | 132.8 | R | nd | S | 31.25 | R | nd |
| *Burkholderia multivorans* (CBC 022) | 3.9 | 7.8 | 132.8 | >132.8 | R | nd | S | 7.81 | R | nd |
| *Burkholderia cenocepacia* (CBC 033) | 3.9 | 15.61 | 132.8 | >132.8 | R | nd | R | nd | S | 31.25 |
| *Burkholderia cenocepacia* (CBC 029) | 3.9 | 15.62 | >132.8 | >132.8 | R | nd | R | nd | S | 15.62 | nd = non-determined
R = resistant,
I = intermediate,
S = sensible (according to the criteria set up by the Clinical and Laboratory Standards Institute (CLSI)
Meropenem (<4 µg/ml S, 8 µg/ml I, >16 µg/ml R)
CFZ (<8 µg/ml S, 16 µg/ml I, >32 µg/ml R)
T (<4 µg/ml S, 8 µg/ml I, >16 µg/ml R)
[a]Isolates recovered from patients with chronical infections Example 5

Cytotoxicity Assay

For assaying the cytotoxicity of the compounds obtained in Examples 1 and 2, cell viability by vital coloration exclusion with Trypan blue (3). The studies were performed using the monocyte cell line THP-I. The IC50 value was defined as the highest drug concentration at which 50% of the cells are viable as compared with the control.

These studies indicated that the assayed compounds have a low to moderate cytotoxicity level (H-BDF: IC50=15.25 µg/mL; H-DBF: IC50 132.5 µg/mL). The Selectivity Index (SI) was determined, defined as the ratio between the MIC value and the IC50 value.

The bacterial isolates used in this invention belonged to the bacterial collection at CINDEFI CAMPA (Colección Argentina de Microorganismos Patógenos y Ambientales). They were recovered from sputum samples of patients treated at La Plata Children Hospital "Sor Maria Ludovica" in the context of scientific collaboration for identifying and characterizing organisms from the *Burkholderia cepacia* complex from clinic samples (1,2). The collaboration followed the Guidelines approved by the Institutional Committee for Review of Research Protocols.

REFERENCES (1) Martina, P., S. Feliziani, C. Juan, M. Bettiol, B. Gatti, O. Yantorno, A. M. Smania, A. Oliver, A. Bosch. 2014. Int. J. Med. Microbiol. 304:1182.

(2) Oderiz, M. J., M. Palau, P. Palacio, M. C. Lewis, M. P. Bettiol, P. Martina, A. Bosch, O. M. Yantorno, B. M. Gatti. 2011. Revista argentina de microbiologia 43:168.

(3) Bonifacio, J. S. Current Protocols in Cell Biology. 2000. John Wiley & Sons Inc, New York.

(4) CLSI, 2011. Supplement M100-S21, Clinical ed. Pennsylvania, USA.

(5) Orme, I. 2001. Antimicrob Agents Chemother. 45: 1943

The invention claimed is:

1. An antibacterial compound of formula I

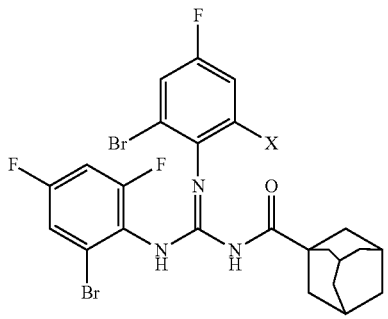

wherein X is selected from fluoro or bromo.

2. A process for preparing the antibacterial compound of claim 1, said process comprising the steps of:
   a) adding an amine and trietilamine to an acyl thiourea in solvent;
   b) slowly adding $HgCl_2$ to the mixture of step a); and
   c) allowing the reaction to proceed at room temperature for at least 6 hours.

3. The process of claim 2, wherein the acyl thiourea has the formula II

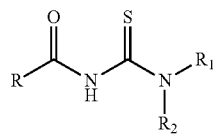

wherein R is the adamantyl group $C_{10}H_{15}$; R1 is H and R2 is 2-Br-4,6-$F_2$—$C_6H_2$.

4. The process of claim 2, wherein the solvent comprises dimethylformamide.

5. The process of claim 2, wherein steps a) and b) are carried out under agitation and overheating is avoided using refrigeration means.

6. The process of claim 2, wherein the amine of step a) is $R_3$—$NH_2$, wherein $R_3$ is selected from the group comprising 2-bromo-4,6-difluoro-phenyl (2-Br-4,6-$F_2$—$C_6H_2$) and 2,6-dibromo-4-fluoro-phenyl (2,6-$Br_2$-4-F—$C_6H_2$).

7. The process of claim 2, wherein after step c) the obtained guanidine is purified by performing the additional steps of:
   d) removing by filtration the HgS formed during the reaction, which is an highly insoluble solid;
   e) removing by filtration the $Et_3NH^+Cl^-$ salt, which is the other solid formed during the reaction, by an extraction process consisting of water addition and ethyl acetate to the reaction mixture under vigorous agitation;
   f) allowing to settle and separating the ethyl acetate organic layer;
   g) optionally, repeating the extraction process of steps e) and f);
   h) drying the organic phase by adding $MgSO_4$ or $CaCl_2$ and removing the solvent under negative pressure;
   i) the obtained solid is purified by standard ethanol re-crystallization methods.

8. A bactericidal pharmaceutical composition comprising the compound of claim 1.

9. A bactericidal pharmaceutical composition against Gram positive bacteria comprising the compound of claim 1.

10. A bactericidal pharmaceutical composition for the treatment of infections affecting patients suffering from cystic fibrosis, said composition comprising the compound of claim 1.

11. A bactericidal pharmaceutical composition for the treatment of infections caused by non-fermenting multiresistant Gram negative bacteria, said composition comprising the compound of claim 1.

* * * * *

UNITED STATES PATENT AND TRADEMARK OFFICE
CERTIFICATE OF CORRECTION

PATENT NO. : 10,857,110 B2  
APPLICATION NO. : 16/324509  
DATED : December 8, 2020  
INVENTOR(S) : Aamer Saeed Bhatti et al.

Page 1 of 1

It is certified that error appears in the above-identified patent and that said Letters Patent is hereby corrected as shown below:

On the Title Page

In (73) Assignee, change the first assignee from "CONSEJO NACIONAL DE INVESTIGACIONES CIENTIFICAS Y TÉCNICAS (CONICENT), Ciudad Autónoma de Buenos Aires, (AR)" to --CONSEJO NACIONAL DE INVESTIGACIONES CIENTIFICAS Y TÉCNICAS (CONICET), Ciudad Autónoma de Buenos Aires, (AR)--.

Signed and Sealed this  
Twenty-first Day of December, 2021

Drew Hirshfeld  
*Performing the Functions and Duties of the*  
*Under Secretary of Commerce for Intellectual Property and*  
*Director of the United States Patent and Trademark Office*